United States Patent
Sonehara et al.

(10) Patent No.: US 8,040,515 B2
(45) Date of Patent: Oct. 18, 2011

(54) FLUORESCENCE DETECTION APPARATUS AND METHOD, AND PRISM USED THEREIN

(75) Inventors: Tsuyoshi Sonehara, Kokubunji (JP); Takashi Anazawa, Koganei (JP); Kenko Uchida, Tokyo (JP); Tomoyuki Sakai, Kokubunji (JP)

(73) Assignee: Hitachi High-Technologies Corporation, Tokyo (JP)

( * ) Notice: Subject to any disclaimer, the term of this patent is extended or adjusted under 35 U.S.C. 154(b) by 597 days.

(21) Appl. No.: 12/051,245

(22) Filed: Mar. 19, 2008

(65) Prior Publication Data

US 2008/0239311 A1    Oct. 2, 2008

(30) Foreign Application Priority Data

Mar. 28, 2007    (JP) .................................. 2007-084262

(51) Int. Cl.
    *G01N 21/25*    (2006.01)
(52) U.S. Cl. ........................................................ 356/417
(58) Field of Classification Search .................. 356/445, 356/417, 246
    See application file for complete search history.

(56) References Cited

U.S. PATENT DOCUMENTS

| | | | | |
|---|---|---|---|---|
| 4,678,326 A | * | 7/1987 | Harjunmaa | 356/73 |
| 4,920,275 A | * | 4/1990 | Itoh | 356/338 |
| 5,313,264 A | * | 5/1994 | Ivarsson et al. | 356/73 |
| 6,215,549 B1 | * | 4/2001 | Suzuki et al. | 356/445 |
| 6,570,657 B1 | * | 5/2003 | Hoppe et al. | 356/445 |
| 6,710,870 B1 | * | 3/2004 | Marowsky et al. | 356/317 |
| 6,775,003 B2 | | 8/2004 | Ivarsson | |
| 2001/0026943 A1 | * | 10/2001 | Dickopf et al. | 422/82.05 |
| 2004/0066510 A1 | * | 4/2004 | Hoff et al. | 356/317 |
| 2010/0111768 A1 | * | 5/2010 | Banerjee et al. | 422/82.08 |

FOREIGN PATENT DOCUMENTS

JP    2004-527741    9/2004

OTHER PUBLICATIONS

"Imaging of Single Fluorescent Molecules and Individual ATP Turnovers by Single Myosin Molecules in Aqueous Solution" by T. Funatsu, et al. Nature, vol. 374, Apr. 1995.

* cited by examiner

*Primary Examiner* — Kara E Geisel
(74) *Attorney, Agent, or Firm* — Mattingly & Malur, PC

(57) ABSTRACT

In order to provide a fluorescence detection apparatus having a high sensitivity, a high processing capacity and a competitive edge in cost, the fluorescence detection apparatus according to this invention irradiate the sample with light so that the aspect ratio of the form of the irradiated region by light on the arrangement surface of the sample may be 1±0.1. The preferable form of irradiate region is not limited to one and varies to some extent depending on the item to be optimized. The form of irradiated region may be, for example, a circle, an equilateral triangle, a square, a regular hexagon and the like.

8 Claims, 11 Drawing Sheets

FLUORESCENCE DETECTION APPARATUS AND METHOD, AND PRISM USED THEREIN

CLAIM OF PRIORITY

The present application claims priority from Japanese application JP 2007-084262 filed on Mar. 28, 2007, the content of which is hereby incorporated by reference into this application.

FIELD OF THE INVENTION

The present invention relates to a fluorescence detection apparatus and method for detecting the fluorescence radiated from spots arranged on the substrate and a prism body used therein.

BACKGROUND OF THE INVENTION

In a fluorescence detecting apparatus, for example, an evanescent field is created on the surface of the substrate by the total internal reflection of light in the optically transparent substrate and biological molecules marked with fluorescence by a probe in the liquid sample supplied on the surface of the substrate are excited in the evanescent field. And the fluorescence radiated from the biological molecules as a result thereof are detected to detect qualitatively biological molecules or to analyze qualitatively the same.

Regarding such a detection of fluorescence, Funatsu et al., Nature vol. 374, 555-559 (1995) describes an apparatus that irradiates a prism with a laser beam and causes the total internal reflection of the laser beam to create an evanescent field in the sample solution on the prism, collects and detects the fluorescence radiating from the biological molecules within the sample excited by the evanescent field with an objective lens. Since an evanescent field is localized on the surface of a prism, the region where fluorescence or scattered light is excited in the sample solution is limited to the vicinity of the surface of the prism. As a result, the background light is contained low, and the molecules near the surface can be detected with a very high sensitivity. As a matter of fact, Funatsu et al., Nature vol. 374, 555-559 (1995) describes the success of detecting a single fluorescent molecule.

And JP-T No. 2004-527741 describes an apparatus that detects emission of light from molecules marked by fluorescence by exciting an evanescent field by having the excited beam totally reflected on the surface of a transparent body.

Generally in order to obtain a total internal reflection, beams must be irradiated obliquely on the reflecting surface. FIG. 1 shows a cross sectional view along the plane of incidence of how the excited beam 3 is irradiated from the inside of the substrate 1 having optical transparency into the boundary face between the substrate 1 and the sample 2 contiguous thereto to be totally reflected thereby. Here, the term "plane of incidence" means a surface drawn along the optical axis of the incident beam and the normal of the boundary surface, and the angle formed by the normal of the boundary surface and the optical beam of the incident beam is called "incident angle." If the refractive index of the substrate 1 is represented by $n_1$, the refractive index of the sample by $n_2$ and the incident angle by $\theta$, the necessary and sufficient condition for inducing a total internal reflection is shown by the following equation.

$$\sin \theta > (n_2/n_1) \quad \text{(Equation 1)}$$

If this condition for a total internal reflection is satisfied, an evanescent field 5 is created only near the boundary surface in the sample. Incidentally, since in the case of a transparent material in the visible range, $n_1 < 2.5$, and in the case of a aqueous solution sample, $n_2 > 1.3$, always $(n_2/n_1) > 0.5$. Therefore, if the equation 1 is satisfied, $\theta > 30°$. Since with ordinary glass n1 to 1.5, in most cases $\theta \geq 60°$. Actually, in Funatsu et al., Nature vol. 374, 555-559 (1995), $\theta = 68°$.

And in Funatsu et al., Nature vol. 374, 555-559 (1995), the beam outputted by gas laser, having passed through the lens, is irradiated obliquely. Generally, the cross section of the beam outputted by gas laser is circular, and even if a beam having a circular section is made to pass through a lens, its section remains circular. When a beam having a circular cross section is irradiated on a reflection surface with an incident angle $\theta$, the irradiated region on the reflection surface turns into an ellipse with an aspect ratio of $\cos \theta$. Therefore, the region irradiated with an excited beam in the apparatus described in Funatsu et al., Nature vol. 374, 555-559 (1995) is an ellipse with an aspect ratio of $\cos 68° = 0.37$. In Funatsu et al., Nature vol. 374, 555-559 (1995), a quartz substrate with $n_1 = 1.46$ is used. As described above, even if whatever material may be used, the total internal reflection occurs always when $\theta > 30°$ and in most cases $\theta > 60°$. Therefore, as far as the same configuration as Funatsu et al., Nature vol. 374, 555-559 (1995) is used, whatever substrate material may be used, the irradiated region always turns out to be an ellipse with an aspect ratio of less than $\cos 30° = 0.86$, and in most cases less than $\cos 60° = 0.5$.

SUMMARY OF THE INVENTION

The field of vision of an objective lens for collecting fluorescence from the irradiated region is generally a circle, in other words an ellipse whose aspect ratio is 1. If an attempt is made to observe a large number of fluorescent spots at the same time, it is preferable to make the maximum use of the field of vision of the objective lens. Therefore, the whole field of vision of the objective lens should be irradiated with light.

However, the irradiated region mentioned in JP-T No. 2004-527741 or Funatsu et al., Nature vol. 374, 555-559 (1995) is in the shape of an ellipse different from the aspect ratio of 1. Therefore, the irradiated region in this case bulge out of the field of vision of the objective lens. In comparison with the case where the field of vision of the objective lens and the irradiated region agree completely, an excitation with the same intensity requires a stronger exciting power, and in the case of excitation with the same total power, the intensity of excitation will diminish. A decline in excitation intensity directly leads to a diminution of signal-noise ratio (S/N) of detection of fluorescence, and this is not allowed in a situation where an ultra-high sensitivity of being able to detect a molecule is required.

On the other hand, any increase in excitation power leads to a higher cost, and this is not preferable for a practical art. Even if a cost increase may be allowed, in the case of measuring fluorescent spots extending over a plurality of fields of vision by scanning the substrate, the irradiation of the regions outside the scope of vision leads to bleaching in some fluorescent spots before they are observed. This means an effective decline in the degree of agglomeration of spots. Such an elliptical irradiation region with a significant difference between its aspect ratio and 1 is not preferable.

This invention was made in view of such a situation, and realizes a fluorescence detection apparatus with a high sensitivity, a high processing capacity (capable of observing a large number of fluorescent spots at the same time) and superiority in terms of cost.

In order to solve the problem described above, the fluorescence detection apparatus according to this invention irradiates the sample with light in such a way that the aspect ratio of the form of irradiated region in the arranging surface for samples with light may be 1±0.1. The preferable form of irradiated region is not limited to one, and varies to some extents depending on the item to be optimized. The shape of irradiated region may be a circle, an equilateral triangle, a square, a regular hexagonal and the like. Incidentally, the term "aspect ratio" mentioned here means the aspect ratio of the ellipse when the irradiated region is approximate to the ellipse to which it is the most similar. Therefore, in this specification, the term "aspect ratio" is used when the irradiated region is shaped other than a circle or an ellipse.

In other words, the fluorescence detection apparatus according to this invention includes a sample arranging unit for arranging liquid sample including transparent bodies having optical transparency, a light source for irradiating the sample arranging surface of the sample arranging unit with light at the predetermined incident angle, and a light detecting unit for detecting fluorescence radiating from the liquid sample by the irradiation of light from the light source, wherein the aspect ratio of the region irradiated by light in the sample arranging surface is 1±0.1.

And the characteristics of this invention shall be clarified by the detailed description of preferred embodiments of this invention and the attached drawings hereto.

According to this invention, it is possible to make the maximum use of the power of excitation beam and the field of vision of the objective lens, and as a result to realize an apparatus having a high processing capacity and a high sensitivity at a low cost. And it is also possible to eliminate bleaching of the fluorescent body outside the field of vision before observation.

DETAILED DESCRIPTION OF THE PREFERRED EMBODIMENTS

Figure 1:
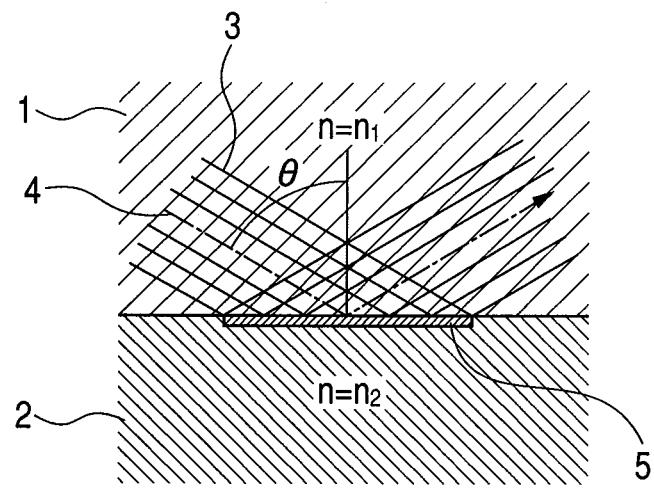
FIG. 1 is a sectional view of a plane of incidence in the ordinary total internal reflection condition.

We will describe below the embodiments of this invention with reference to attached drawings. However, it should be noted that these embodiments are only examples of realizing this invention, and that they do not limit the application of this invention. And in each drawing the common elements are marked by the same reference code.

<Principle of this Invention>

In order to maximize the number of independent fluorescent spots observable at the same time (maximize the processing capacity), the radiation region of a shape obviously matching completely with the field of vision of the objective lens, in other words, a circular radiation region is preferable.

On the other hand, since circles cannot fill completely a flat surface, when fluorescent spots fixed within a range wider than the field of vision of the objective lens are observed by scanning the substrate, it is difficult to raise the ratio of the observation region to the substrate surface (effective observation ratio) to 100 percent. It is possible to rescan the gap between various circles. However, in that case the ratio of making the best use of the field of vision of the objective lens falls down.

Accordingly, from the viewpoint of improving the effective observation ratio, shapes that can fill completely a flat surface, in other words, triangle, square, and hexagon are effective. Among them, the shapes high in the ratio of making the best use of the field of vision of an objective lens are obviously circle, equilateral triangle, square, and regular hexagon. Therefore, it is preferable to choose the shape of irradiated region from among circle, equilateral triangle, square, regular hexagon and the intermediate shapes among these keeping in mind the ratio of making best use of the field of vision of the objective lens and effective observation ratio of the substrate. When these preferable shapes are comprehensively expressed, one arrives at shapes whose aspect ratio is effectively 1.

Now, while the meaning of the term "aspect ratio" for ellipse or rectangle is obvious, it is not so in the case of a parallelogram that is neither a triangle nor a rectangle. Therefore, we will define below the aspect ratio generalized for any randomly chosen shape. For this purpose, we will in the first place introduce the concept of correlation coefficient between an irradiated region and an elliptical region.

An orthogonal coordinate system whose starting point is the center of the irradiated region is set on the irradiation surface, and the distribution of irradiation intensity is represented by I (x, y). In the case of a uniform distribution of radius w, the distribution of irradiation intensity (x, y) can be expressed as follows:

$$I(x, y) = \begin{cases} I_0 & (x^2 + y^2 \leq w^2) \\ 0 & (x^2 + y^2 > w^2) \end{cases} \quad \text{(Equation 2)}$$

And in the case of an elliptic Gaussian whose radius of major axis is $w_x$, and whose radius of minor axis is $w_y$, the distribution of radiation intensity I(x, y) is as follows:

$$I(x, y) = I_0 \exp\left(-\frac{2x^2}{w_x^2} - \frac{2y^2}{w_y^2}\right) \quad \text{(Equation 3)}$$

Here, the region E of an ellipse is substituted as follows:

$$J(x, y) \equiv \begin{cases} 1 & ((x, y) \in E) \\ 0 & ((x, y) \notin E) \end{cases} \quad \text{(Equation 4)}$$

At this time, the correlation coefficient r between the irradiated region and the ellipse E is defined by the following equation.

$$r \equiv \frac{\int I(x, y) J(x, y) \, dx \, dy}{\sqrt{\int (I(x, y))^2 \, dx \, dy \int (J(x, y))^2 \, dx \, dy}} \quad \text{(Equation 5)}$$

By a Cauchy-Schwarz inequality $r \leq 1$, and when the irradiated region and the ellipse have completely agreed r=1. The aspect ratio of any randomly chosen irradiated region is defined as the aspect ratio of the ellipse that maximizes the correlation coefficient r with the irradiated region. If the distribution of irradiation intensity is uniform, and provided that
S: area of the region contained in both the irradiated region and the ellipse,
$S_1$: area of the irradiated region
$S_2$: area of the ellipse
The correlation coefficient r will be as follows:

$$r = \frac{S}{\sqrt{S_1}\sqrt{S_2}} \quad \text{(Equation 6)}$$

Figure 2:
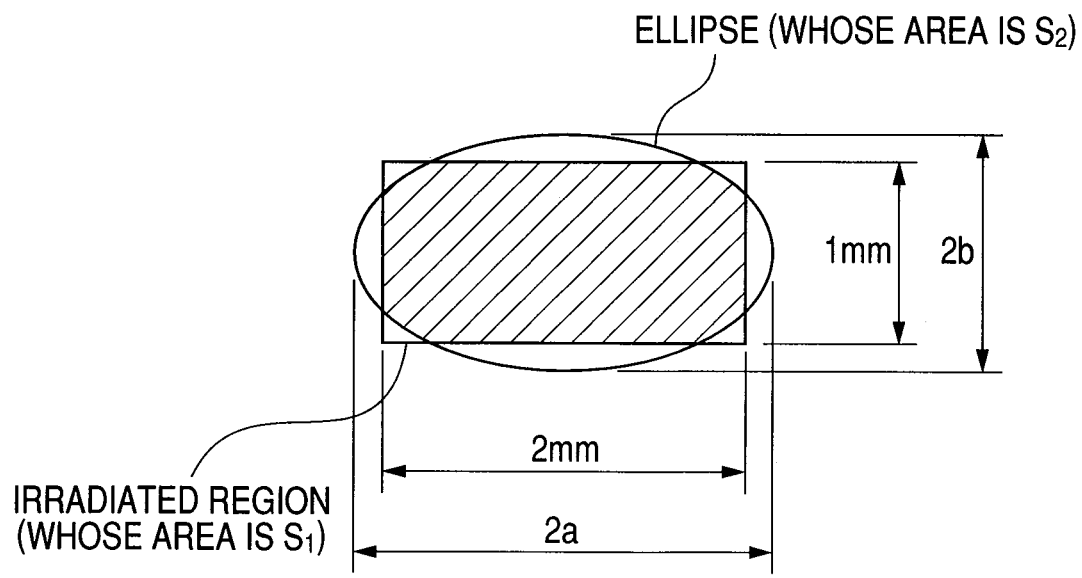
FIG. 2 is an illustration showing the relationship between an irradiated region and an ellipse.
Figure 3:
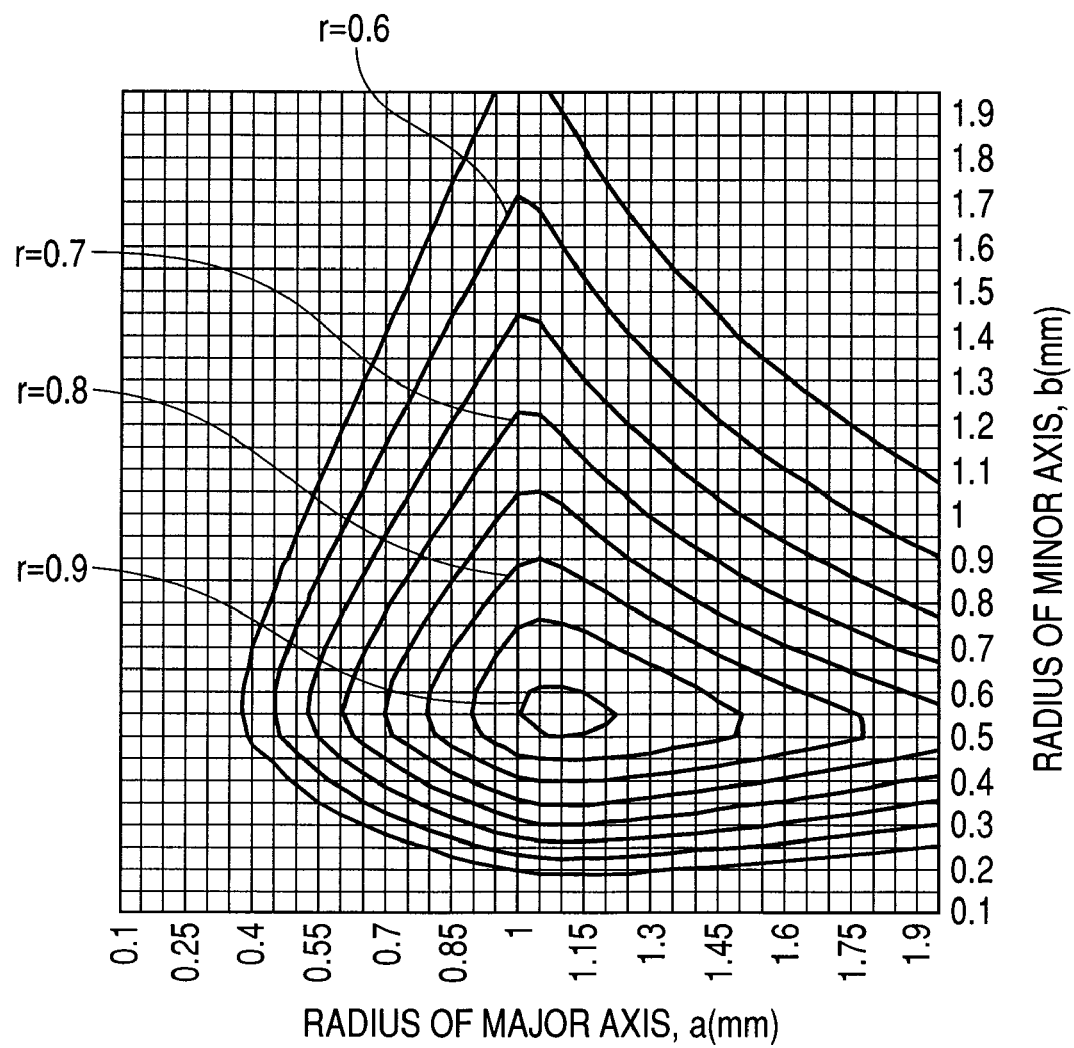
FIG. 3 is a graph showing the correlation coefficient for a rectangle with a longer side 2 mm long and a shorter side 1 mm long.
Figure 4:
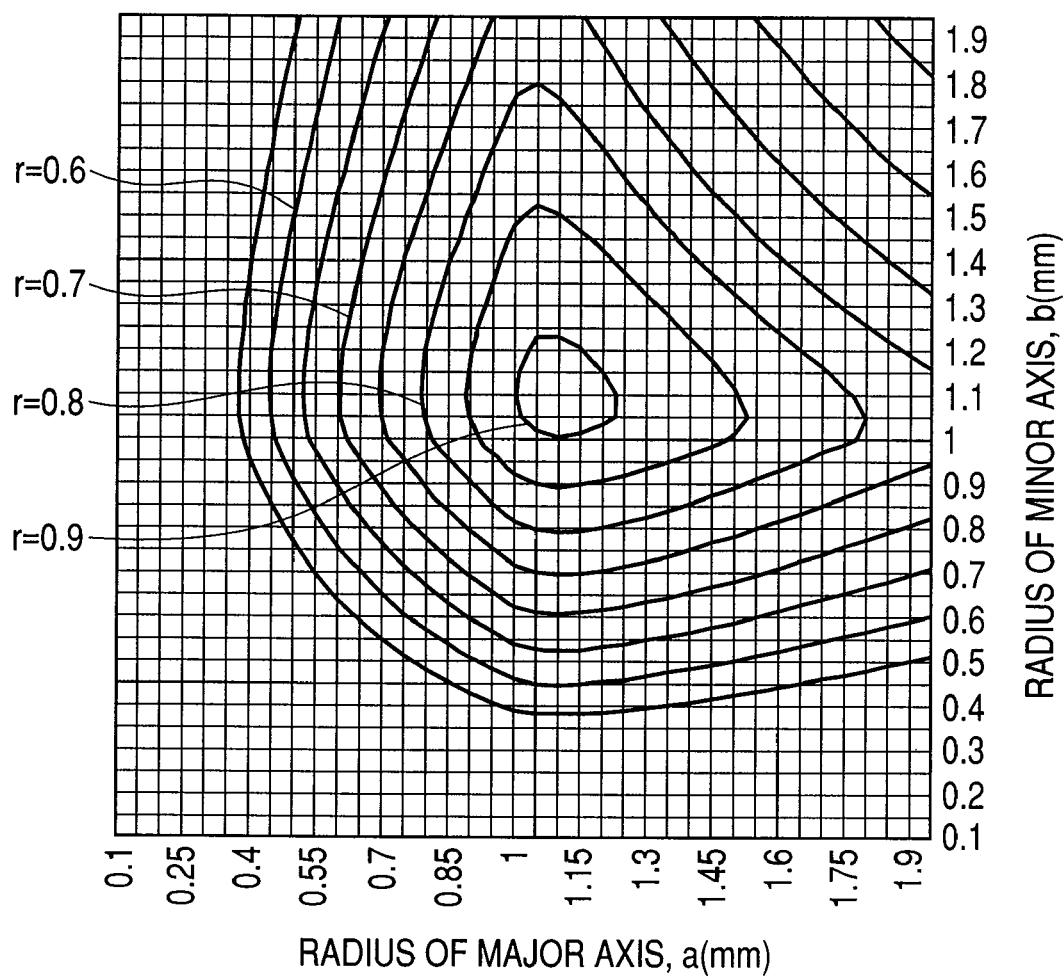
FIG. 4 is a graph showing the correlation coefficient for a square with a side 2 mm long.

FIG. 2 is a figure showing an ellipse and the common region between the ellipse and the irradiated region when the irradiated region is a rectangle whose longer side is 2 mm long and shorter side is 1 mm long. The shaded portion is the common region. In this case, since the irradiated region is rectangular, one understands instinctively that its aspect ratio is 2. And FIG. 3 shows with a contour the relationship between the radius a of major axis and the radius b of minor axis of an ellipse and the correlation coefficient r defined by the equation 6. As FIG. 3 shows clearly, when a=1.12, b=0.56, r has the maximum value of 0.92. Therefore, the aspect ratio defined as "the major axis/minor axis of the ellipse that maximizes the correlation coefficient" turns out to be 1.12/0.56=2, which agrees with the instinctive aspect ratio. Furthermore, FIG. 4 shows the relationship of correlation coefficient r between the radius a of major axis and the radius b of minor axis of the ellipse when the irradiated region is a square a side of which is 2 mm long. In this case, the correlation coefficient is the maximum when a=b=1.1 mm, and as expected the aspect ratio of the irradiated region turns out to be 1. For irradiated regions not rectangular and of an ordinary shape, the aspect ratio can be defined as the radius of major axis/radius of minor axis of an ellipse that maximizes the correlation coefficient defined in the equation 5 or the equation 6, and its value is 1 for a regular hexagon and an equilateral triangle.

Incidentally, there are roughly speaking two means of bringing effectively the aspect ratio of the irradiated region to 1. One is to irradiate a beam having the section of the predetermined aspect ratio other than 1 that is determined according to the incident angle. Another means is to provide a blackout coating having an aperture whose aspect ratio is 1 near the substrate surface. We will describe in details below the former method with reference to drawings.

Figure 5:
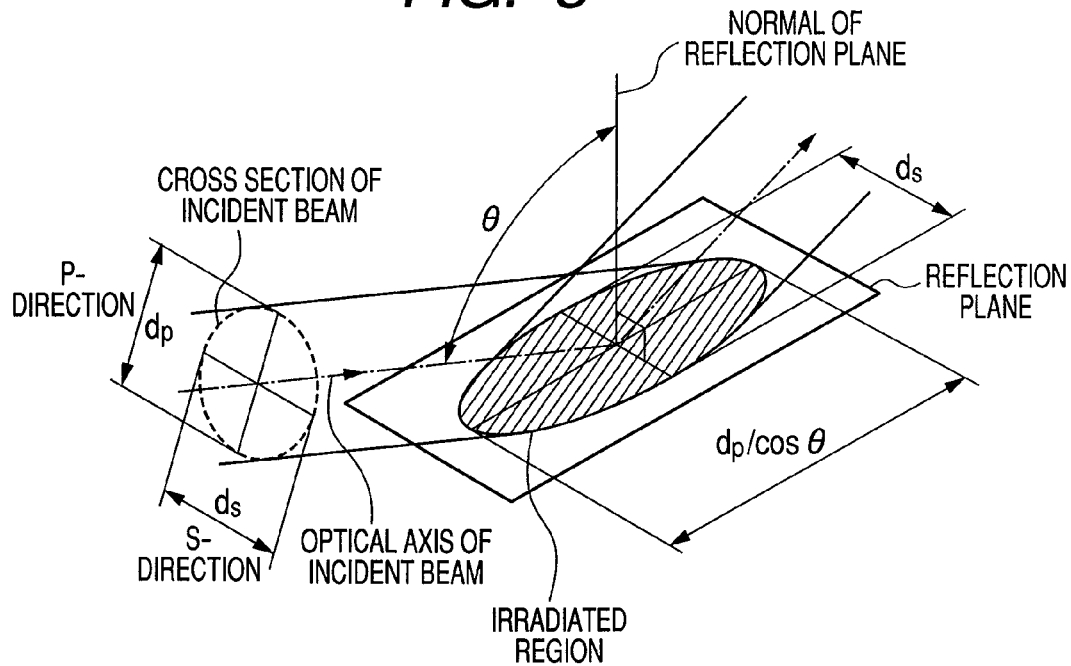
FIG. 5 is a perspective view showing the condition of a total internal reflection.

FIG. 5 is a figure showing in three dimensions the aspect of total internal reflection. In FIG. 5, the cross section of the incident beam is elliptical, but evidently it can take other shapes such as a rectangle. In any case, the beam section has two measurements, length in the parallel direction (p direction) with the plane of incidence and length in the vertical direction (s direction) to the plane of incidence. When the length in the p direction is represented by dp and the length in the s direction by ds, the ordinary circular beam is naturally represented by dp=ds. The irradiated region has also measurements in two directions, length in the direction of the plane of incidence and length vertical to the plane of incidence. The length in the plane of incidence direction is dp/cos θ and the length in the vertical direction to the plane of incidence is ds. Therefore, by bringing the aspect ratio in the cross section of the incident beam to dp/ds=cos θ, the aspect ratio of the irradiated region can be brought to 1.

We will describe below various embodiments of the fluorescence detection apparatus to which such principle of this invention is applied.

First Embodiment

Figure 6:
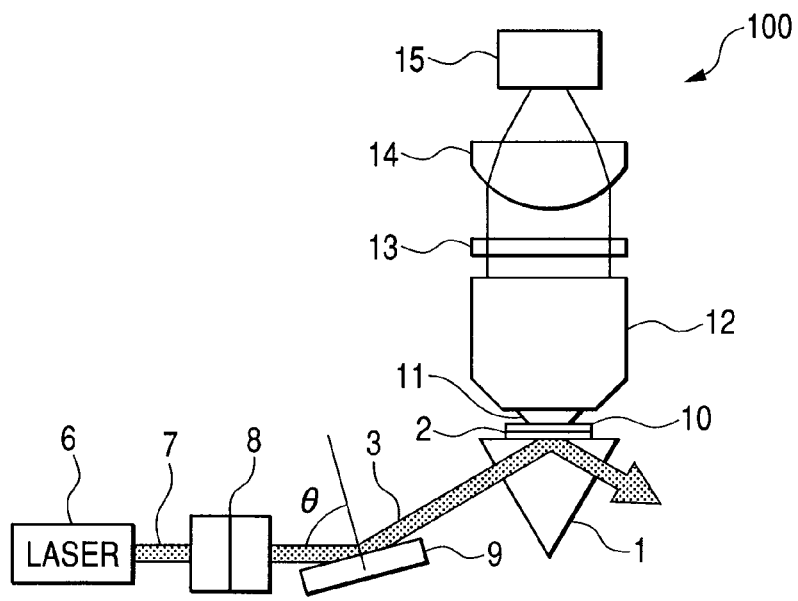
FIG. 6 is a side view showing the schematic configuration of the fluorescence detection apparatus according to the first embodiment of this invention.

FIG. 6 is a side view of showing the schematic configuration of the fluorescence detection apparatus 100 according to the first embodiment of this invention. The fluorescence detection apparatus includes a laser light source (hereinafter referred to as "light source") 6, a beam cross section shaping unit 8 for shaping the incident beam to the predetermined shape, a mirror 9 for reflecting the beam in the predetermined direction, a transparent body 1 for performing the function of a triangular prism and that of the substrate for mounting the sample 2, a cover glass 10 for covering the sample 2, an objective lens 12 for collecting and collimating the irradiated fluorescence, a filter 13 for removing the scattered light element contained in the fluorescence, an imaging lens 14 and a detector 15 (for example, CCD and CMOS sensors).

In the fluorescence detection apparatus 100 having such a configuration, the output beam 7 from the light source 6, after passing through the beam cross section shaping unit 8 composed of a pair of anamorphic prism, is reflected by the mirror 9. And the reflected light by the mirror 9 penetrates into the transparent body 1 and is totally reflected by the boundary face between the sample 2 and the transparent body 1. The fluorescent molecule in the sample is excited by an evanescent field generated in the sample to irradiate a fluorescent light 11. The fluorescent light 11, after passing through the cover glass 10, is collected and collimated by the objective lens 12. The collimated fluorescent light, after passing through the filter 13 and removing the scattered light component, is imaged on the light-sensitive surface of the detector 15 by the imaging lens 14. Incidentally, in this embodiment, it is possible to use the second harmonic laser of ND-YAG that outputs a circular beam 0.4 mm in diameter and with a wavelength of 532 nm as the light source 6.

Figure 7:
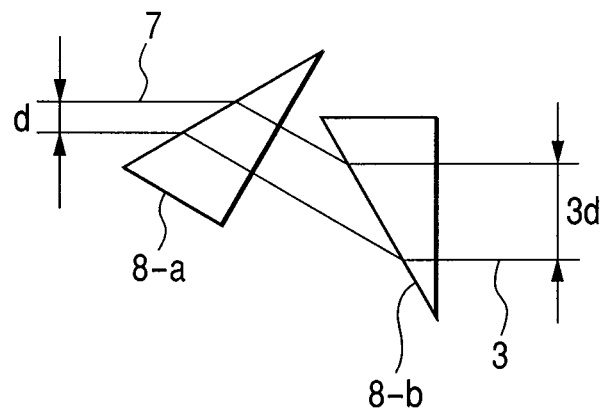
FIG. 7 is an illustration showing the configuration of the beam cross section shaping unit 8.

FIG. 7 is a front view showing the schematic configuration of the beam cross section shaping unit 8. The beam cross section shaping unit 8 is a pair of anamorphic prisms constituted by two prisms. By the refraction in the two prisms, the cross section of the output beam of the beam cross section shaping unit has the same diameter in the vertical direction as the input beam and has a diameter in the horizontal direction for example triple of the input beam. Since the cross section of the input beam is a circle 0.4 mm in diameter, the output beam will be an elliptical beam whose diameter in the vertical direction is 0.4 mm and the same in the horizontal direction is 1.2 mm. This beam is reflected in the predetermined direction by the mirror 9, and irradiates vertically on the plane of incidence of the transparent body 1 in the form of a triangular prism, irradiates the horizontal reflection surface at an incident angle of 70.5 degrees to cause a total internal reflection.

Figure 8:
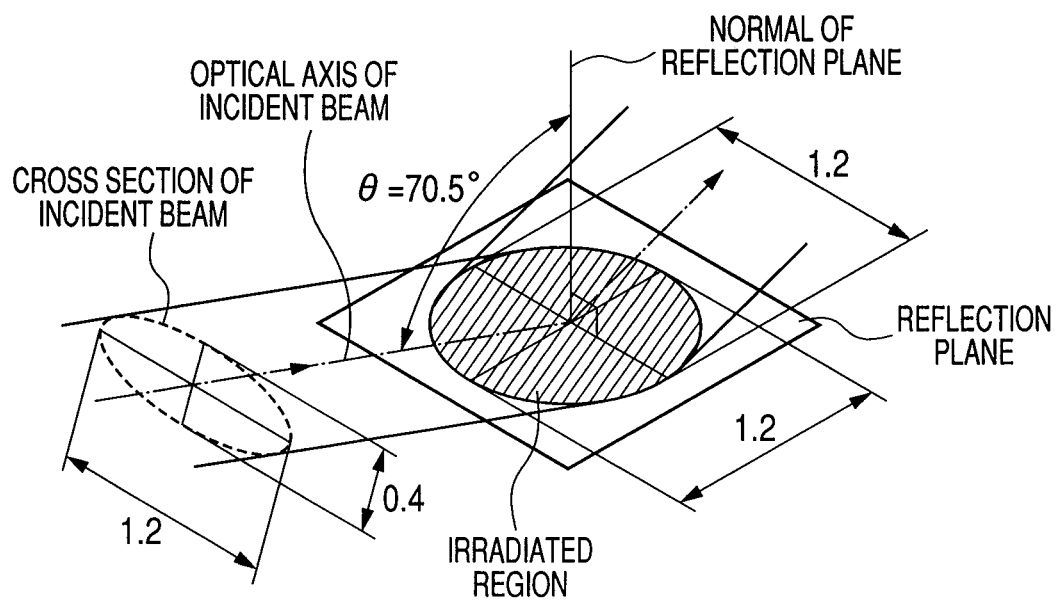
FIG. 8 is an enlarged perspective view showing around the irradiated region according to a first embodiment.

Therefore, when expressed by the codes shown in FIG. 5, an incident beam with ds=1.2 mm and dp=0.4 mm irradiates the plane of incidence at an incident angle of $\theta$=70.5°, and the irradiated region on the reflection surface is ds=1.2 mm long in the s direction, and dp/cos $\theta$=0.4 mm/cos 70.5°=1.2 mm long in the p direction. Thus, the form of the irradiated region is a circle. Incidentally, an enlarged perspective view around the irradiated region is shown in FIG. 8.

And as for the objective lens 12, for example one with an effective scope in the form of a circle 1.2 mm in diameter and a 20-power magnification can be used. As a result, the scope of the objective lens and the irradiated region match perfectly, and the fluorescent molecules within the scope of vision can be wholly observed at the same time, and a high sensitivity of being able to detect even a single fluorescent molecule can be obtained with the minimum exciting power.

Figure 9:
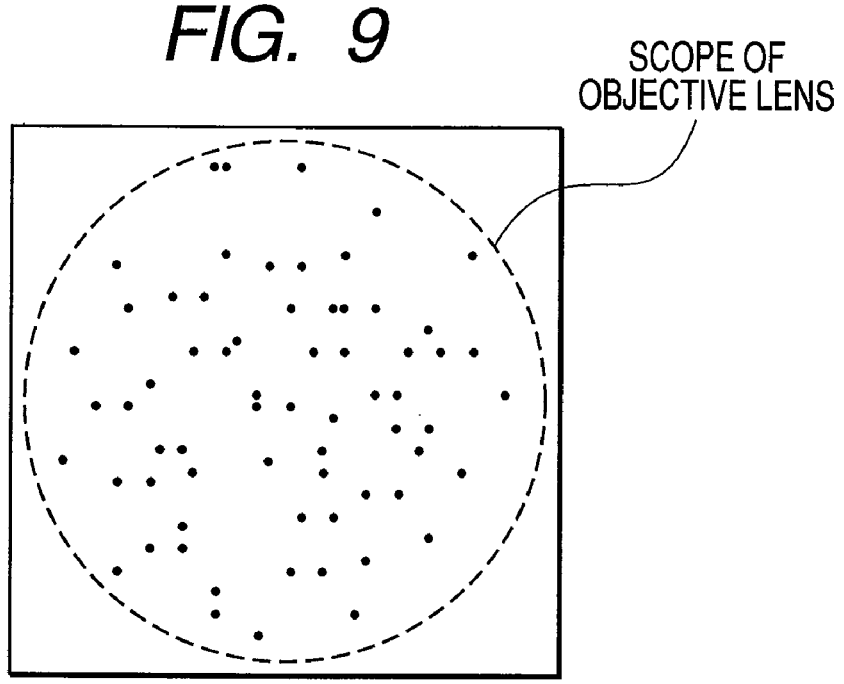
FIG. 9 is an illustration showing a fluorescent image obtained by the fluorescence detection apparatus according to the first embodiment.

FIG. 9 is an illustration showing a fluorescent spot image obtained by the fluorescence detection apparatus 100 according to this embodiment. In this embodiment, probe molecules subject to unite with the fluorescence units contained in samples 2 are fixed at random on the substrate (transparent body 1).

In this embodiment, for example, a laser for outputting a beam with a circular cross section of 0.4 mm in nominal diameter is used, and the guaranteed value of aspect ratio of the output beam cross section is 1±0.1. Generally, the guaranteed value of the nominal circular cross section of the beam outputted by a laser is approximately 1.0±0.1. Accordingly, in this invention, if the aspect ratio is 1±0.1, a high sensitivity and a high processing capacity can be guaranteed. And since with this aspect ratio it is possible to control sufficiently the shaping precision of the beam cross section shaping unit 8 and the precision of incident angle, the precision of aspect ratio of the laser output beam will be the precision of aspect ratio of the irradiated region ultimately obtained. Therefore, an aspect ratio of 1.0±0.1 can be considered effectively as an aspect ratio of 1.

Figure 10:
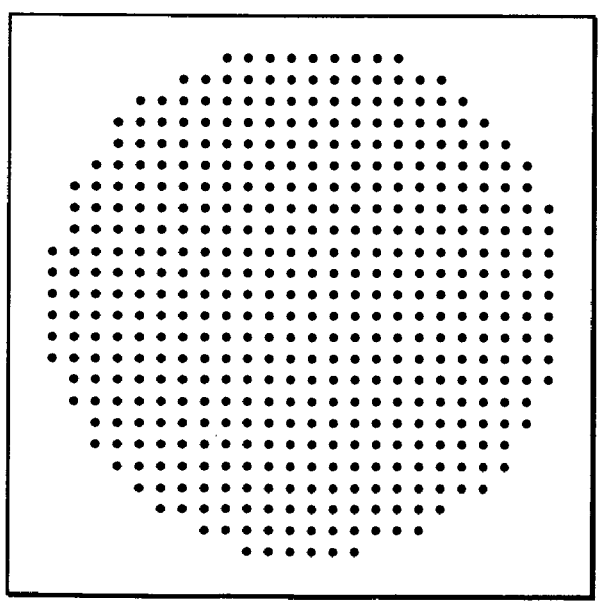
FIG. 10 is an illustration showing a fluorescent image of probe molecules arranged in the reticular pattern on the substrate according to the first embodiment.
Figure 11:
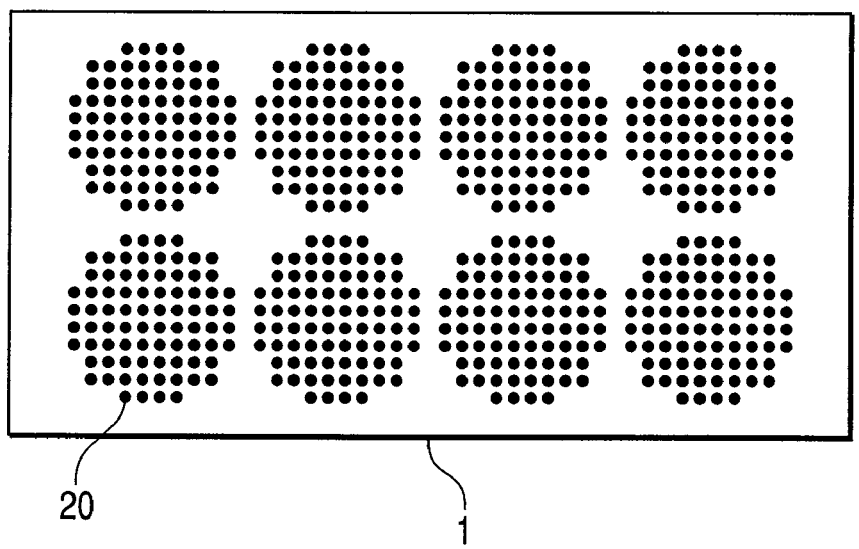
FIG. 11 is an illustration showing the example 1 of the arrangement of probe molecules on the substrate.

FIG. 10 is an illustration showing another fluorescent spot image obtained by the fluorescence detection apparatus 100 according to this embodiment. As shown in FIG. 10, the probe molecules are fixed in a reticular pattern on the substrate. As a result, the density of fluorescent spots observable in the scope of vision improved by approximately a digit and at the same time the processing capacity per unit length of time improved by approximately a digit. FIG. 11 shows schematically the arrangement of probe molecules on the substrate. In this embodiment, due to the circular form of the irradiate region, the probe molecules are fixed only in a plurality of circles arranged on the lattice.

Figure 12:
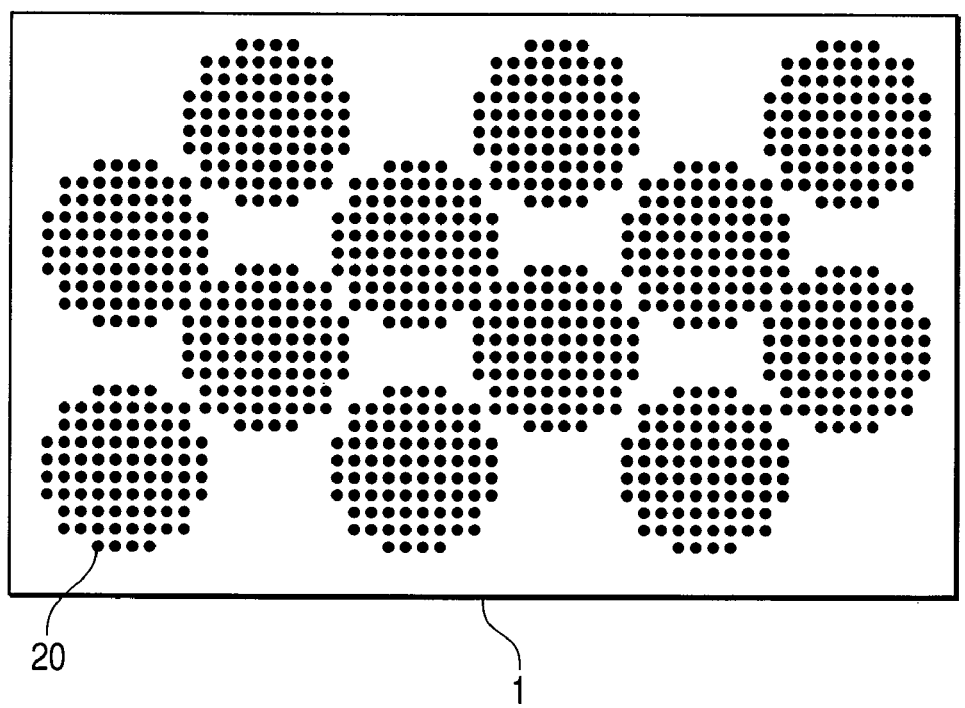
FIG. 12 is an illustration showing the example 2 of the arrangement of probe molecules on the substrate.
Figure 13:
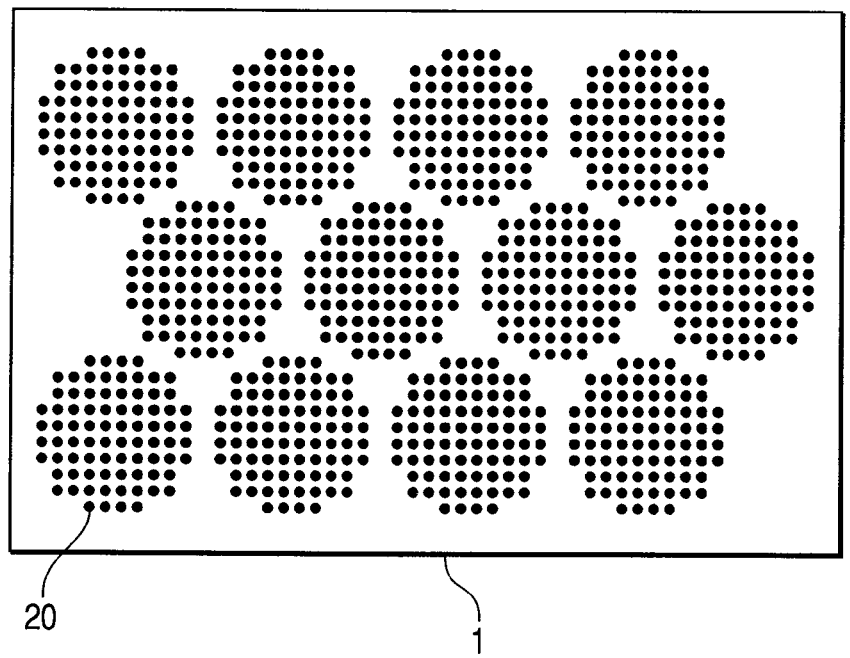
FIG. 13 is an illustration showing the example 3 of the arrangement of probe molecules on the substrate.

Incidentally, while in FIG. 11 circles are arranged in a reticular pattern on the substrate, their arrangement in zigzag as shown in FIG. 12 or in the hexagonal closest packing mode as shown in FIG. 13 improves the efficiency of utilizing the substrate surface, and the effect of being able to save scanning time by several tens of percent can be further obtained.

Second Embodiment

Figure 14:
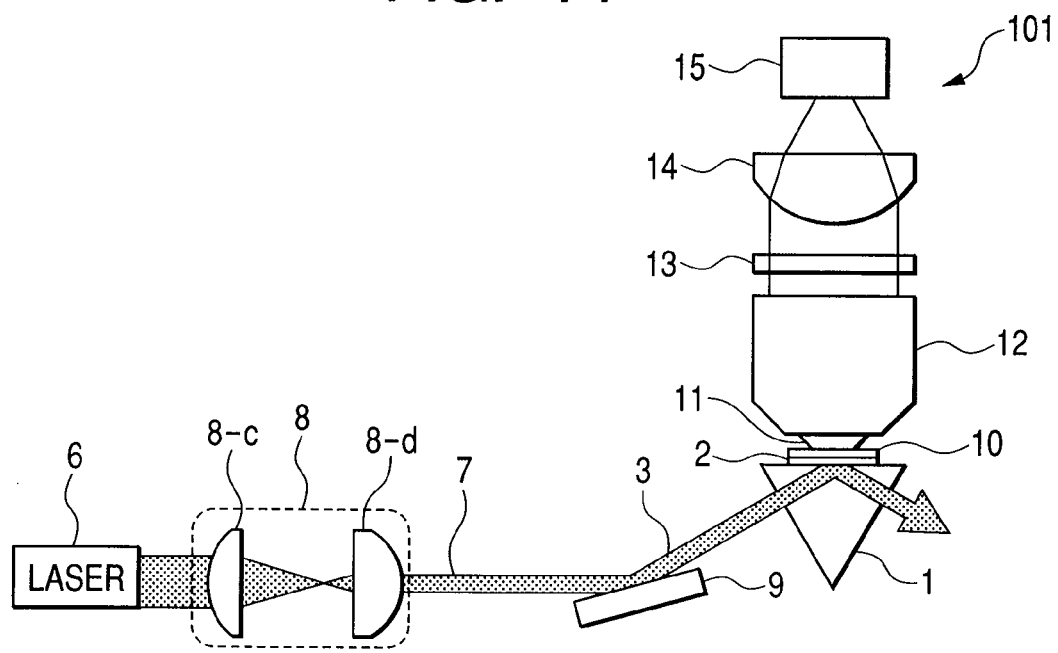
FIG. 14 is a side view showing the schematic configuration of the fluorescence detection apparatus according to a second embodiment of this invention.

FIG. 14 is a side view showing the schematic configuration of the fluorescence detection apparatus 101 according to the second embodiment of this invention. The fluorescence detection apparatus 101 has basically the same configuration as the fluorescence detection apparatus 100 according to the first embodiment. However, an aspherical lens without rotational symmetry around the optical axis is used in the place of an anamorphic prism as the beam cross section shaping unit 8.

In this embodiment, a cylindrical lens 8-c with a focal distance of 75 mm and a cylindrical lens 8-d with a focal distance of 25 mm are used as the beam cross section shaping unit 8. And this converts a circular laser output beam 1.2 mm in diameter to a beam ds=1.2 mm and dp=0.4 mm. In this embodiment, the beam cross section length is converted only in the p direction (see FIG. 5). However, it is possible to convert both beam cross section lengths by using an aspherical lens having curvature in two directions.

The intrinsic effect of the fluorescence detection apparatus 101 having the configuration of this embodiment is that the anamorphic prism can only enlarge the beam cross section while the cylindrical lens can both enlarge and reduce the same. Therefore, the latter can facilitate the adjustment of the size of the irradiated region.

Third Embodiment

Figure 15:
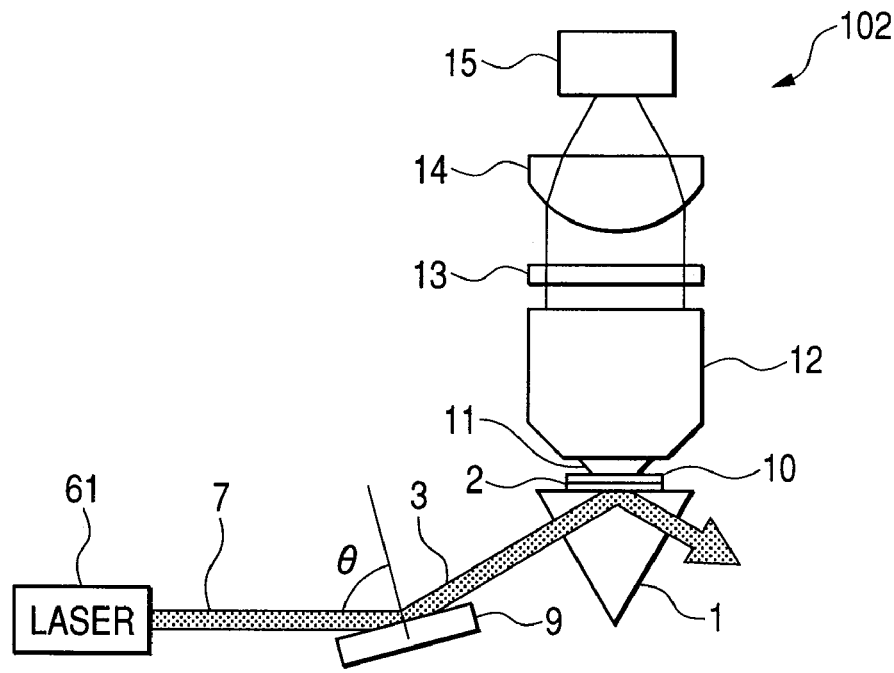
FIG. 15 is a side view showing the schematic configuration of the fluorescence detection apparatus according to a third embodiment of this invention.

FIG. 15 is a side view showing the schematic configuration of the fluorescence detection apparatus 102 according to the third embodiment of this invention. The fluorescence detection apparatus 102 has basically the same configuration as the fluorescence detection apparatus 100 according to the first embodiment. However, it has no beam cross section shaping unit 8 and uses a semiconductor laser outputting a beam whose section has an aspect ratio of 0.33 as a light source 61. It is possible to bring the aspect ratio of the irradiated region to 1 without any beam cross section shaping unit by using a laser that outputs a beam having a cross section whose aspect ratio is cos $\theta$ against the incident angle $\theta$ for total internal reflection.

According to this embodiment, the configuration of the fluorescence detection apparatus is simplified, and has the effect of reducing the cost.

Fourth Embodiment

Figure 16:
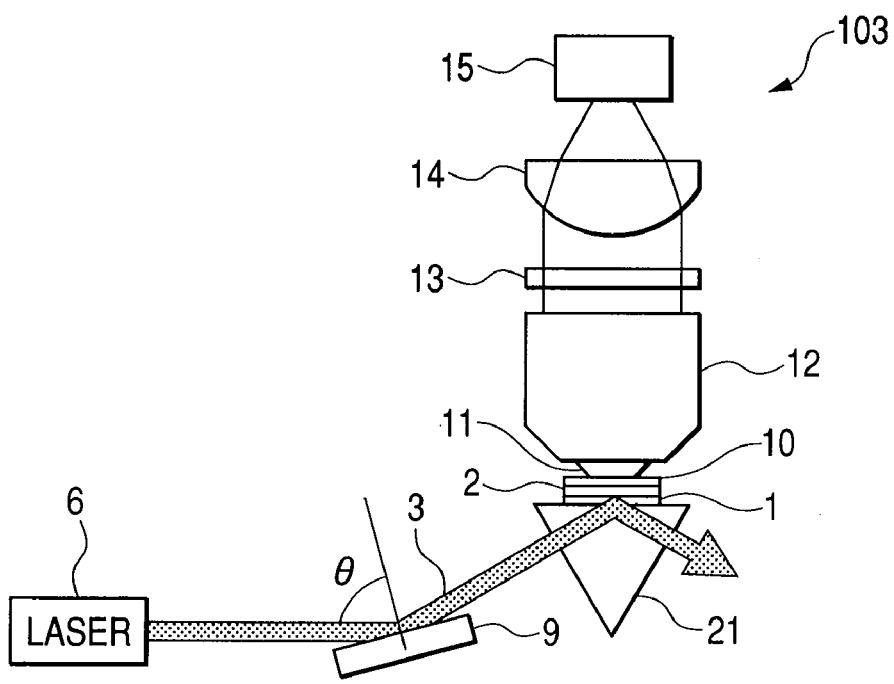
FIG. 16 is a side view showing the schematic configuration of the fluorescence detection apparatus according to a fourth embodiment of this invention.
Figure 17:
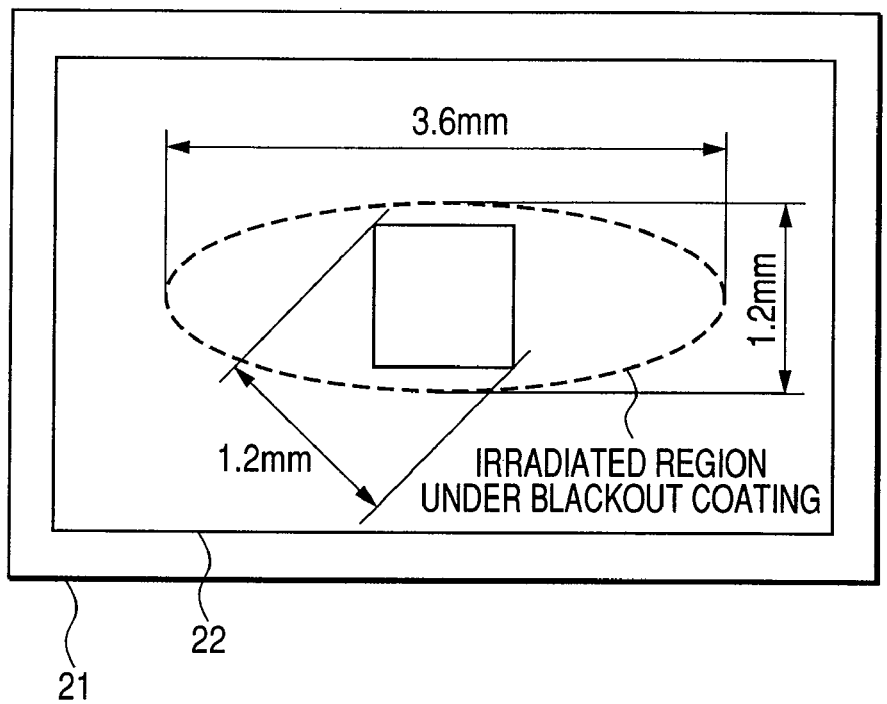
FIG. 17 is an illustration showing an example of constitution of a transparent body 21 on which a blackout coating has been formed.

FIG. 16 is a side view showing the schematic configuration of the fluorescence detection apparatus 103 according to the fourth embodiment of this invention. The fluorescence detection apparatus 103 has no beam cross section shaping unit 8 and like the first embodiment uses the second harmonic laser that outputs a beam with a circular cross section (aspect ratio of 1±0.1) as the light source 6. And while the transparent body 1 serves also as the substrate for mounting the sample and prism in the first to third embodiments, the substrate 1 on which the probe molecules are fixed and the prism 21 for total internal reflection are separated in the fourth embodiment. In other words, both are provided as separate members. And on the top surface (surface on which the substrate is mounted) of the prism 21, the blackout coating (Al or preferably Cr) 22 like the one shown in FIG. 17 is formed by vapor deposition or spattering. And a matching liquid of the same refraction index with the substrate 1 is inserted between the prism 21 and the substrate 1. This assures that no total internal reflection occurs on the top surface of the prism 21 and that the total internal reflection occurs on the sample arranging surface of the substrate 1. The other aspects of configuration are the same as FIG. 6.

In the fluorescence detection apparatus 103 shown in FIG. 16 having the configuration described above, the beam having a circular cross section of 1.2 mm in diameter outputted by the light source 6 is irradiated as it is into the prism 21 without any shaping of the cross section. On the upper surface of the prism 21, as shown in FIG. 17, a blackout coating provided with a square aperture with a diagonal line of 1.2 mm long is formed. As a result, the beam irradiated region turns out to be, as shown in FIG. 17, an ellipse with an aspect ratio of 0.33. However, on the surface of the substrate 1, it will be a square inscribed in a circle of 1.2 mm in diameter. As a result, it is possible to obtain the effect of being able to observe all the fluorescent spots arranged compactly on the lattice on the substrate 1 with a 100% efficiency. In other words, by adopting square beam irradiated regions, it is possible to arrange the probe molecules at regular intervals without creating wastes in space on the substrate 1. On the other hands, the adoption of circular beam irradiated regions as shown in FIGS. 11 to 13 results in waste of space in the arrangement of probe molecules on the substrate 1. Therefore, it is clear that making the best efforts in designing the blackout coating 22 in relation to the form of the beam irradiated regions is technically very effective.

Figure 18:
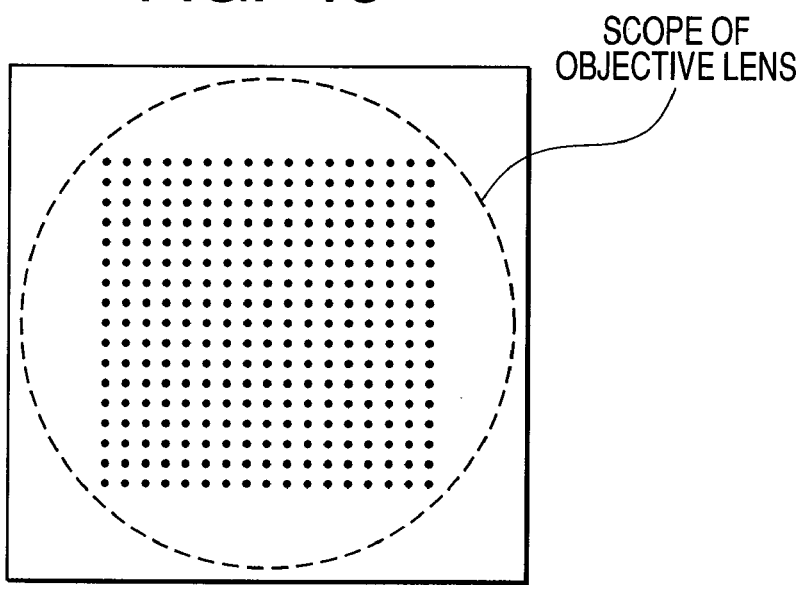
FIG. 18 is an illustration showing a fluorescent image obtained by the fluorescence detection apparatus according to the fourth embodiment.

FIG. 18 shows an example of fluorescent spot image obtained by the fluorescent detection apparatus 103. In this embodiment, we have chosen a square aperture in the blackout coating 22, but other forms whose aspect ratio is 1 can be adopted. Incidentally, according to the configuration of this embodiment, the laser power irradiated on the portion out of the aperture is wasted, but this system has an effect of facilitating the control of the form of irradiated region. As far as a beam cross section shaping unit is used to shape beam cross section as in the case of the first embodiment, it is difficult to obtain polygonal and other similar forms of irradiated region. However, this embodiment has an effect of facilitating the acquisition of tetragonal or hexagonal irradiated regions.

Figure 19:
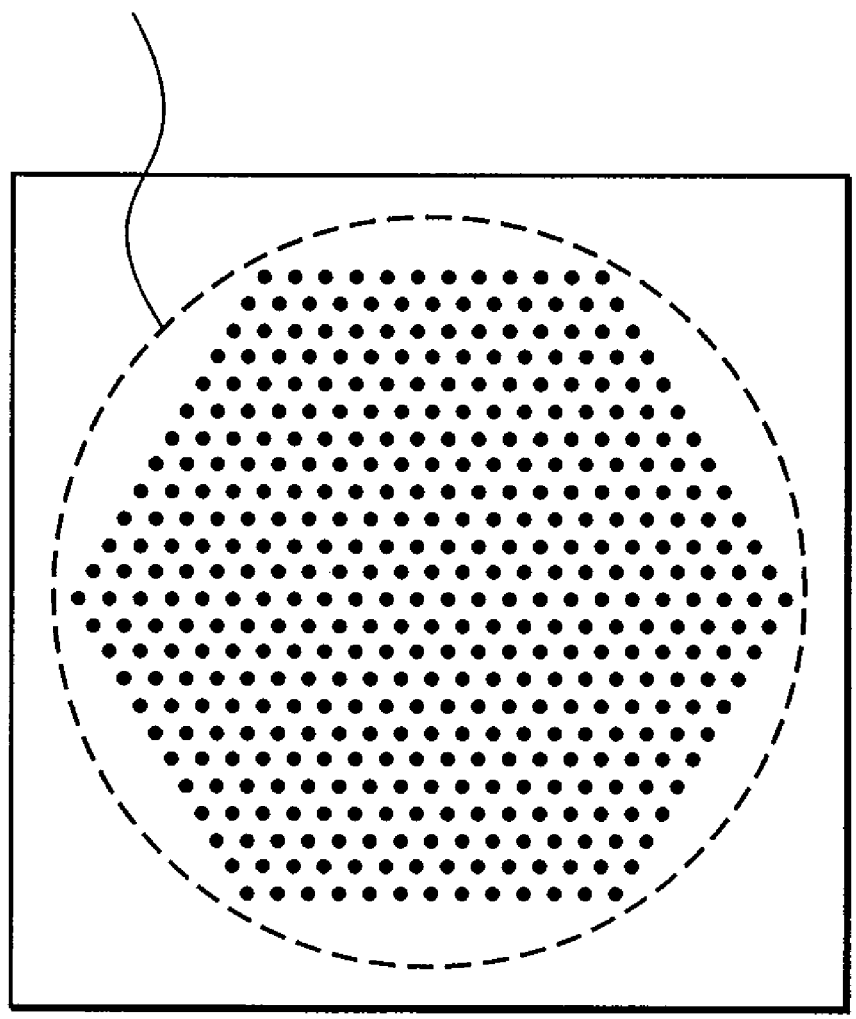
FIG. 19 is an illustration showing an example of fluorescent spot image when the form of aperture in the blackout coating is a regular hexagon.

Furthermore, FIG. 19 shows an example of the fluorescent spot image obtained when a hexagonal form is chosen for the form of the aperture in the blackout coating 22. This improves the use ratio of the scope of the objective lens by 30 percents as compared with the case wherein the form of aperture chosen is square. In other words, as the comparison of FIG. 18 and FIG. 19 reveals clearly, hexagon represents a larger share by 30 percent of the form of fluorescent spot image in the scope of the objective lens.

CONCLUSION

The fluorescent detection apparatus by various embodiments of this invention can be applied to a DNA sequencer based on the use of extension reactions, a total internal reflection fluorescence-type DNA microarray reader and the like.

As described above, in the fluorescence detection apparatus according to this embodiment, the sample is irradiated with light in such a way that the aspect ratio of the form of the irradiated region by light on the arranging surface of samples may be 1±0.1 while satisfying the conditions for total internal reflection so that an evanescent field may be generated in the sample solution. By so doing, it is possible to detect with a high sensitivity and at the same time much fluorescence from the sample. And the radiation energy can be used efficiently, and therefore excess excitation energy will be unnecessary and the apparatus cost can be reduced.

The preferable form of irradiated region is not limited to one, and depending on the item to be optimized, this varies to a certain extent. The form of irradiated region may be, for example, a circle, an equilateral triangle, a square, a regular hexagon and the like. Therefore, it is possible to arrange samples without leave any space among them on the substrate and to improve the processing capacity by using square or hexagonal irradiated regions. Incidentally, in order to choose a non-circular form for the irradiated regions, it is enough to provide a blackout coating with an aperture of the predetermined form (square, hexagon, equilateral triangle, or the like) on the side of arranging samples of the transparent body (prism). By providing such a prism body, it is possible to realize a high-sensitivity, high-processing-capacity and low-cost fluorescence detection apparatus by fixing the improved prism body according to this invention to a conventional fluorescence detection apparatus.

To form effectively circular irradiated region, if the light source is a laser for outputting light with a circular cross section, it is enough to use a beam cross section shaping unit to shape the cross section form from a circle to an ellipse. This beam cross section shaping unit is constituted by a pair of prisms, and leaves the light from the light source in the vertical direction as it is and magnifies the same only in the horizontal direction to the predetermined magnification. Or it is constituted by an aspherical lens without rotational symmetry around the optical axis of the light coming from the light source. Since it is possible to form circular irradiated regions without requiring such a complicated configuration, it is possible to provide a high-sensitivity and high processing capacity fluorescence detection apparatus without raising the cost of the apparatus. Incidentally, it is possible to constitute from the beginning the light source with a semiconductor laser for outputting the light with an elliptical cross section.

What is claimed is:
1. A fluorescence detection apparatus comprising:
  a sample arranging unit for arranging a liquid sample has a transparent body having optical transparency;
  a light source for irradiating a sample arranging surface of said sample arranging unit with a light at a predetermined incident angle; and
  an optical detection unit for detecting fluorescence radiated by said liquid sample in response to the irradiation of light from said light source,
  wherein a value of (a dimension in a direction parallel to a plane of incidence of a section by a surface vertical to an optical axis of the incident light on said sample arranging surface) /(a dimension in a direction vertical to the plane of incidence of the section by the surface vertical to the optical axis of the incident light on said sample arranging surface) is substantially equal to a cosine function of said incident angle so that an aspect ratio of an irradiated region of light in said sample arranging surface is 1±0.1,
  wherein said sample arranging unit further includes a substrate and the transparent body is covered with a black- out coating having an aperture of a predetermined form and said liquid sample on the side of said sample arranging surface, and wherein the predetermined form of said aperture approximates an ellipse whose major axis and minor axis have a ratio of 1±0.1 in length.

2. The fluorescence detection apparatus according to claim 1, wherein a value of a sine function for said incident angle is greater than (the refractive index of said liquid sample)/ (the refractive index of said sample arranging unit).

3. The fluorescence detection apparatus according to claim 1, wherein said light source is a laser outputting a light with a circular section, and wherein said fluorescence detection apparatus further comprises a beam cross section shaping unit for shaping the cross section form of the light from said light source from circular form to ellipse.

4. The fluorescence detection apparatus according to claim 3, wherein said beam cross section shaping unit includes a pair of prisms that amplify the light from said light source to a predetermined magnifying power only in a horizontal direction.

5. The fluorescence detection apparatus according to claim 3, wherein said beam cross section shaping unit includes an aspherical lens without a property of rotational symmetry with respect to the optical axis of the light from said light source.

6. The fluorescence detection apparatus according to claim 1, wherein said light source is a semiconductor laser outputting a light with an elliptical cross section.

7. The fluorescence detection apparatus according to claim 1, wherein said transparent body serves as a substrate for mounting said liquid sample.

8. A fluorescence detection method for arranging liquid sample, comprising the steps of:

arranging a liquid sample on a sample arranging unit that has a transparent body having an optical transparency;

irradiating the sample arranging surface of said sample arranging unit with light outputted by a light source at a predetermined incident angle; and detecting the fluorescence radiated from said liquid sample in response to the irradiation of light from said light source by means of a light detecting unit, wherein a value of (a dimension in a direction parallel to a plane of incidence of a section by a surface vertical to an optical axis of the incident light on said sample arranging surface) /(a dimension in a direction vertical to the plane of incidence of the section by the surface vertical to the optical axis of the incident light on said sample arranging surface) is substantially equal to a cosine function of said incident angle so that an aspect ratio of an irradiated region of light in said sample arranging surface is 1±0.1, wherein said sample arranging unit further includes a substrate and the transparent body is covered with a blackout coating having an aperture of a predetermined form and said liquid sample on the side of said sample arranging surface, and wherein the predetermined form of said aperture approximates an ellipse whose major axis and minor axis have a ratio of 1±0.1 in length.

\* \* \* \* \*